(12) United States Patent
Montgomery, Jr. et al.

(10) Patent No.: US 7,957,793 B2
(45) Date of Patent: Jun. 7, 2011

(54) METHODS FOR IDENTIFYING NEURONAL SPIKES

(75) Inventors: Erwin B. Montgomery, Jr., Middleton, WI (US); He Huang, Madison, WI (US); John T. Gale, Chestnut Hill, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1566 days.

(21) Appl. No.: 11/315,808

(22) Filed: Dec. 22, 2005

(65) Prior Publication Data
US 2006/0167369 A1 Jul. 27, 2006

Related U.S. Application Data

(60) Provisional application No. 60/638,554, filed on Dec. 22, 2004.

(51) Int. Cl.
*A61B 5/04* (2006.01)
(52) U.S. Cl. ...................................................... 600/544
(58) Field of Classification Search ........... 600/544–547
See application file for complete search history.

(56) References Cited

U.S. PATENT DOCUMENTS

| | | | |
|---|---|---|---|
| 4,461,304 A | 7/1984 | Kuperstein | |
| 5,398,187 A | 3/1995 | Yamada et al. | |
| 5,928,143 A | 7/1999 | McNaughton | |
| 6,011,996 A | 1/2000 | Gielen et al. | |
| 6,066,163 A | 5/2000 | John | |
| 6,128,527 A | 10/2000 | Howard, III et al. | |
| 6,253,109 B1 | 6/2001 | Gielen | |
| 6,301,492 B1 | 10/2001 | Zonenshayn | |
| 6,330,466 B1 | 12/2001 | Hofmann et al. | |
| 6,343,226 B1 | 1/2002 | Sunde et al. | |
| 6,354,299 B1 | 3/2002 | Fischell et al. | |
| 6,366,813 B1 * | 4/2002 | DiLorenzo | 607/45 |
| 6,368,147 B1 | 4/2002 | Swanson | |
| 6,454,774 B1 | 9/2002 | Fleckenstein | |
| 6,459,936 B2 | 10/2002 | Fischell et al. | |

(Continued)

OTHER PUBLICATIONS

Bankman, I.N., Johnson, K.O. and Schneider, W. "Optimal detection, classification, and superposition resolution in neural waveform recordings," IEEE Trans. Biomed. Eng., vol. 40, pp. 836-841, Aug. 1993.

(Continued)

*Primary Examiner* — Charles A Marmor, II
*Assistant Examiner* — Navin Natnithithadha
(74) *Attorney, Agent, or Firm* — Craig A. Fieschko, Esq.; DeWitt Ross & Stevens S.C.

(57) ABSTRACT

A method for identifying neuronal spikes (extracellular action potentials) is described wherein measured microelectrode readings from tissue are reviewed to identify spikes (successive readings having prolonged rises and/or falls). The frequency of such spikes as a function of their amplitude assumes a bimodal distribution wherein higher amplitude spikes represent neuronal spikes (signal) and lower amplitude spikes represent noise, and thus the higher amplitude spikes can be assumed to be neuronal spikes. Neuronal spikes from the same neuron can then be assumed to have substantially the same waveform shape and period, with the only significant difference between them being the scaling of their amplitudes (i.e., the amplitudes of spikes from the same neuron tend to be proportionate at any given time along their period). Thus, by testing identified neuronal spikes for matching timing and for proportional amplitudes, the neuronal spikes may further be identified as coming from the same or different neurons.

27 Claims, 5 Drawing Sheets

U.S. PATENT DOCUMENTS

| | | | |
|---|---|---|---|
| 6,463,328 | B1 | 10/2002 | John |
| 6,484,059 | B2 | 11/2002 | Gielen |
| 6,495,020 | B1 | 12/2002 | Swanson |
| 6,539,263 | B1 | 3/2003 | Schiff et al. |
| 6,567,690 | B2 | 5/2003 | Giller et al. |
| 6,587,724 | B2 | 7/2003 | Mann |
| 6,600,954 | B2 | 7/2003 | Cohen et al. |
| 6,606,521 | B2 | 8/2003 | Paspa et al. |
| 6,662,035 | B2 | 12/2003 | Sochor |
| 6,684,105 | B2 | 1/2004 | Cohen et al. |
| 6,694,162 | B2 | 2/2004 | Hartlep |
| 6,731,986 | B2 | 5/2004 | Mann |
| 6,819,956 | B2 * | 11/2004 | DiLorenzo ............... 607/45 |
| 6,829,498 | B2 | 12/2004 | Kipke et al. |
| 6,892,098 | B2 | 5/2005 | Ayal et al. |
| 7,209,787 | B2 * | 4/2007 | DiLorenzo ............... 607/45 |
| 7,231,254 | B2 * | 6/2007 | DiLorenzo ............... 607/45 |
| 7,242,984 | B2 * | 7/2007 | DiLorenzo ............... 607/45 |
| 7,277,758 | B2 * | 10/2007 | DiLorenzo ............... 607/45 |
| 7,324,851 | B1 * | 1/2008 | DiLorenzo ............... 607/45 |
| 2005/0192646 | A1 * | 9/2005 | Grayden et al. ............ 607/57 |
| 2006/0135862 | A1 * | 6/2006 | Tootle et al. ............. 600/373 |

OTHER PUBLICATIONS

Buchholz, S.R., Montgomery Jr., E.B., Head restraint device for chronic recording of neural activity in the awake monkey. J. Neurosci. Methods, 1988; 25: 139-42.

Chandra, R. and Optican, L.M., "Detection, classification, and superposition resolution of action potentials in multiunit single-channel recordings by an on-line real-time neural network," IEEE Trans. Biomed. Eng., vol. 44, pp. 403-412, May 1997.

Cocatre-Zilgien, J.H. and Delcomyn, F., "A slope-based approach to spike discrimination in digitized data," in Journal of Neuroscience Methods, vol. 33. pp. 241-249, 1990.

Datta S, Datta S. Comparisons and validation of statistical clustering techniques for microarray gene expression data. Bioinformatics 2003;19:459-466.

Deep-Brain Stimulation for Parkinson'S Disease Study Group. Deep-brain stimulation of the subthalamic nucleus or the pars interna of the globus pallidus in Parkinson's disease. N. Eng. J. Med., 2001; 345: 956-63.

Falkenberg, J.H., McNames, J. and Burchiel, K.J. "Statistical methods of analysis and visualization of extracellular microelectrode recordings," Annual International Conference of the IEEE Engineering in Medicine and Biology—Proceedings, Cancun, Mexico, pp. 2515-2518,17-21, Sep. 2003.

Falkenberg, J.H., McNames, J., Aboy, M., Burchiel, K. J., "Segmentation of extracellular microelectrode recordings with equal power," Annual International Conference of the IEEE Engineering in Medicine and Biology—Proceedings, Cancun, Mexico, Sep. 17-21, 2003, pp. 2475-2478.

Gozani, S.N. and Miller, J.P. "Optimal discrimination and classification of neuronal action potential waveforms from multiunit, multichannel recordings using software-based linear filters," IEEE Trans. Biomed. Eng., vol. 41, pp. 358-372, Apr. 1994.

Guedalia I.D., London M., Werman M., An On-Line Agglomerative Clustering Method for Nonstationary Data. Neural Computation 1999;11:521-540.

Hashimoto T., Elder C.M., Vitek, J.L., A template subtraction method for stimulus artifact removal in high-frequency deep brain stimulation. J. Neurosci. Methods, 2002; 113: 181-6.

Hulata E., Segev R., Ben-Jacob E., A method for spike sorting and detection based on wavelet packets and Shannon's mutual information. J. Neurosci. Methods, 2002;117:1-12.

Koller, W., Pahwa, R., Busenbark, K., et al., High-frequency unilateral thalamic stimulation in the treatment of essential and parkinsonian tremor. Ann. Neurol., 1997; 42: 292-9.

Lange, T., Roth, V., Braun, M.L., Buhmann, J.M., Stability-Based Validation of Clustering Solutions, Neural Computation 2004;16:1299-1323.

Lewicki, M.S. (1998) "A review of methods for spike sorting: the detection and classification of neural action potentials." Network: Computation in Neural Systems. 9(4): R53-R78.

Montgomery, Jr.E.B., Baker, K.B., Kinkel, R.P., Barnett, G., Chronic thalamic stimulation of the tremor of multiple sclerosis. Neurology, 1999; 53: 625-8.

Montgomery Jr. E.B., Buchholz Sr. The striatum and motor cortex in motor initiation and execution. Brain Res., 1991; 549: 222-9.

Newby, .PK., Tucker, K.L., Empirically derived eating patterns using factor or cluster analysis: a review. Nutr. Rev. 2004;62:177-203.

Obeid, I. Wolf, P.D., Evaluation of spike-detection algorithms for a brain-machine interface application, IEEE Transactions on Biomedical Engineering, vol. 51, No. 6, Jun. 2004, pp. 905-911.

Quiroga, R. Q., Nadasdy, Z., Ben-Shaul, Y., Unsupervised Spike Detection and Sorting with Wavelets and Superparamagnetic Clustering, Neural Computation. 2004; 16:1661-1687.

Quirk, M.C., Wilson, M.A., Interaction between spike waveform classification and temporal sequence detection. J. Neurosci. Methods, 1999; 94: 41-52. Erratum in J. Neurosci. Methods, 2000; 99: 143-5.

Santiago, R.A., McNames, J., Burchiel, K., Lendaris, G.G., "An automated method for neuronal spike source identification," International Joint Conference on Neural Networks, Portland, Oregon, Jul. 20-24, 2003, pp. 2837-2842.

Santiago, R.A., McNames, J., Burchiel, K., Lendaris, G.G., "Developments in understanding neuronal spike trains and functional specializations in brain regions," Neural Networks, vol. 16, No. 5-6, Jun./Jul. 2003, pp. 601-607.

Stata Reference Manual, Stata Statistical Software Release 7.0. StataCorp: Colleage Station, 1985;1:224-235.

Stitt, J.P., Gaumond, R.P., Frazier, J.L., and Hanson, F.E., Action potential classifiers: a functional comparison of template matching, principal components analysis and an artificial neural network Chemical Senses, vol. 23, No. 5, pp. 531-539, Oxford University Press (1998).

Theodorakis, S., Koutroumbas, K., Pattern Recognition, second ed. Academic Press: Amsterdam, 2003.

Vercuei,L L., Krack, P., Pollak, P., Results of deep brain stimulation for dystonia: a critical reappraisal. Move. Disord., 2002; 17: S89-93.

Wagenaar, D.A., Potter, S.M., Real-time multi-channel stimulus artifact suppression by local curve fitting. J. Neurosci. Methods 2002;120:113-120.

Won, D.S., Chong, D.Y. and Wolf, P.D., "Effects of spike sorting error on information content in multi-neuron recordings," presented at the 1st Int. IEEE EMBS Conf. Neural Engineering, Capri Island, Italy, 2003.

Worgotter, F., Daunicht, W. J. and Eckmiller, R. "An on-line spike form discriminator for extracellular recordings based on an analog correlation technique," in Journal of Neuroscience Methods, vol. 17, pp. 141-151, 1986.

Yang, X. and Shamma, S., "A totally automated system for the detection and classification of neural spikes," IEEE Trans. Biomed. Eng., vol. 35, pp. 806-816, Oct. 1988.

* cited by examiner

FIG. 1
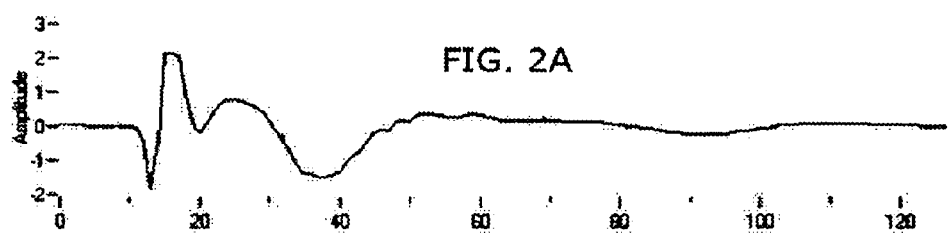
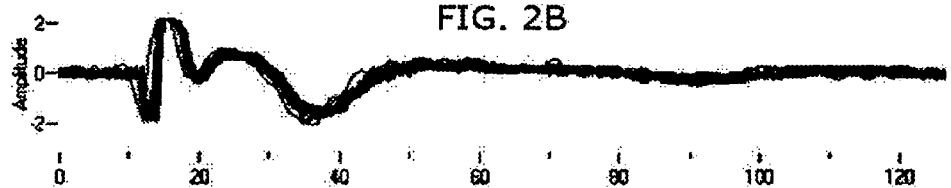

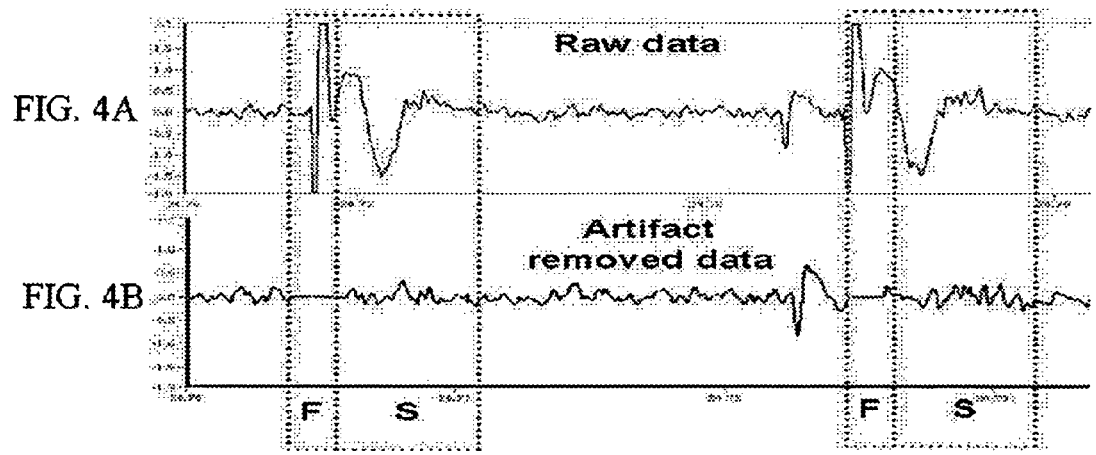
FIG. 4A
FIG. 4B
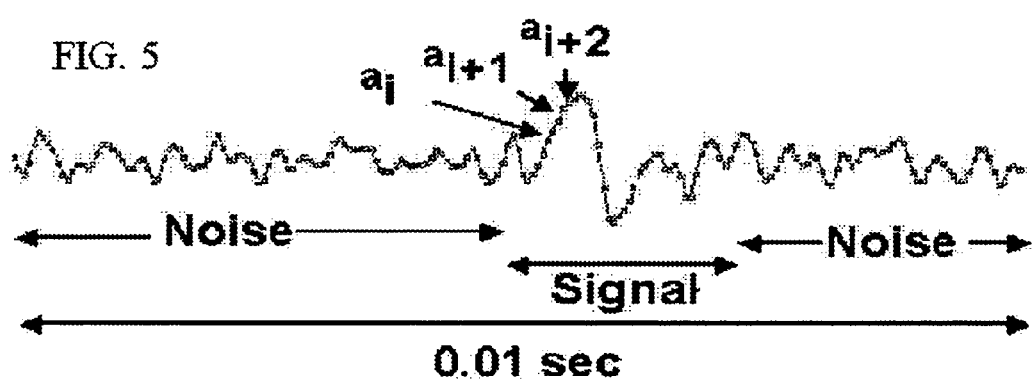
FIG. 5

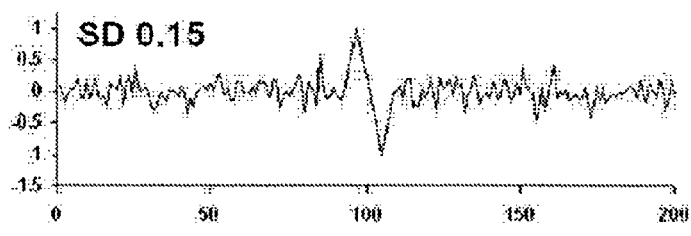
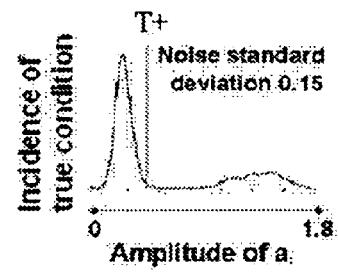
FIG. 6A
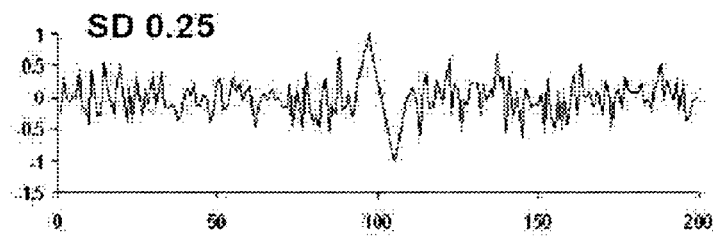
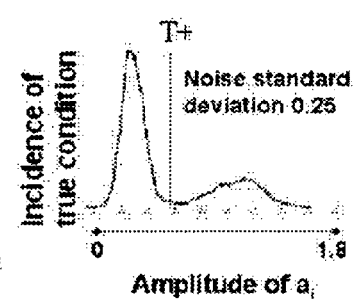
FIG. 6B
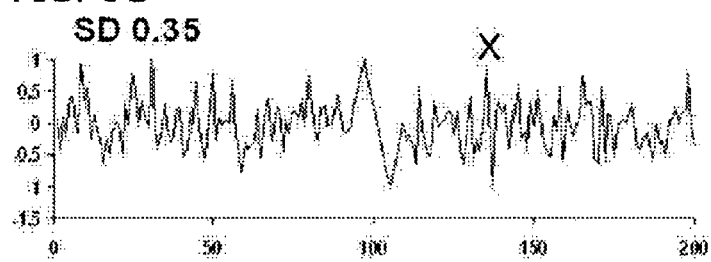
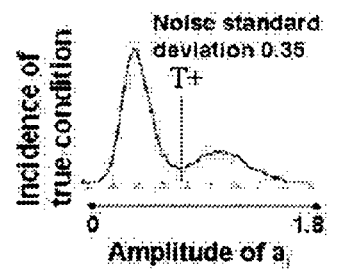
FIG. 6C
FIG. 7
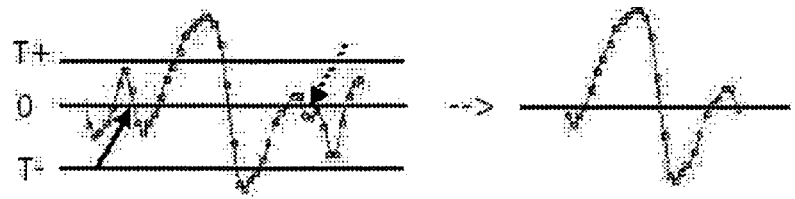

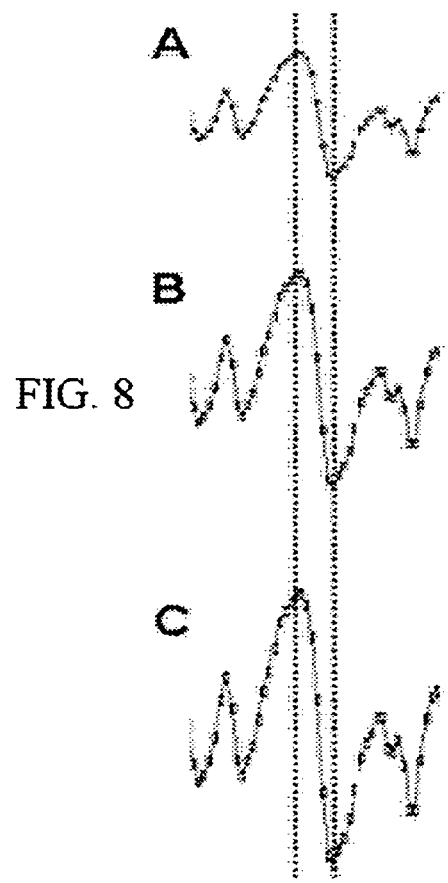
FIG. 8
FIG. 9
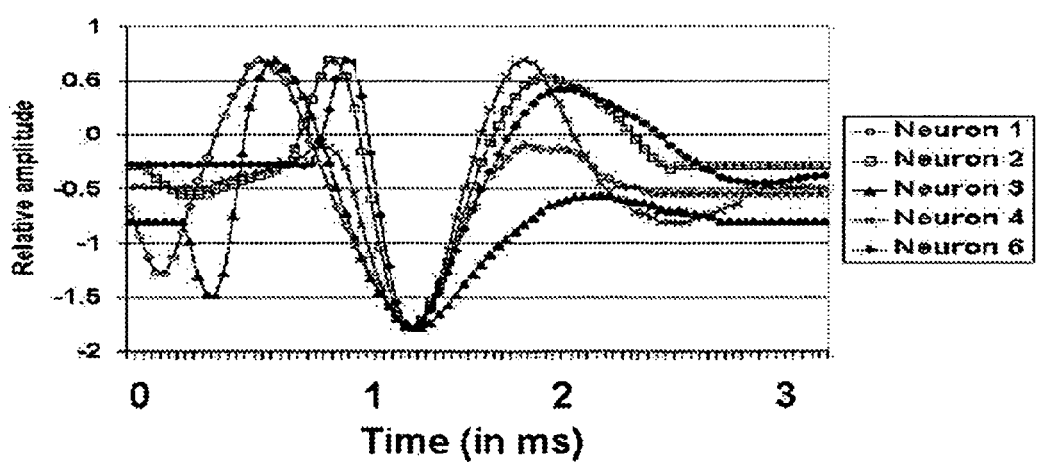

METHODS FOR IDENTIFYING NEURONAL SPIKES

CROSS-REFERENCE TO RELATED APPLICATIONS

This application claims priority under 35 USC §119(e) to U.S. Provisional Patent Application 60/638,554 filed 22 Dec. 2004, the entirety of which is incorporated by reference herein.

FIELD OF THE INVENTION

This document concerns an invention relating generally to methods for interpreting neurological signals, and more specifically to methods for discriminating and sorting signals generated by individual neurons.

BACKGROUND OF THE INVENTION

Deep brain stimulation (DBS) is a methodology wherein therapeutic electrodes are implanted within the brain to deliver timed impulses to desired nerve centers, and can be used to treat a variety of disorders, in particular movement disorders such as Parkinson's disease and dystonia. A major challenge with DBS relates to determination of where to place therapeutic electrodes: while medical imaging (e.g., magnetic resonance imaging) can provide a starting point for identification of placement locations, since the therapeutic electrodes must be precisely placed (e.g., in those regions of the brain giving rise to muscle tremors), it is necessary to obtain a more detailed map of brain structures. A common technique is to advance a needle-like probe (or multiple such probes) into the brain, with each probe bearing one or more reading microelectrodes. The reading microelectrodes measure neuronal activity, as indicated by extracellular action potentials, which are in essence voltage spikes caused by neuronal firings. As readings are taken, the patient—who is generally awake during the procedure—may be requested to perform some action (e.g., move an arm or leg), thereby provoking neuronal firings. By looking at the location of the probe (i.e., probe location and depth) and the characteristics of the measured neuronal spikes (e.g., shape, frequency, etc.), the regions of the brain traversed by the probe can be mapped: spike characteristics can be correlated with those known to exist in certain portions of the brain, changes in spike characteristics can indicate interfaces between different regions of the brain, and so forth. Additionally, stimulating input (voltage) pulses can simultaneously be delivered to regions of the brain which are candidates for electrode implantation to determine their physiological effect (e.g., whether tremors are reduced, whether the patient experiences some change in feeling, etc.), with such stimulating input pulses being delivered via an input point on the probe or via a separate electrode spaced from the probe. Once the map of the brain is generated and candidate locations for implantation of therapeutic electrodes are identified, therapeutic electrodes may be permanently implanted, with the therapeutic electrodes being connected to a power supply which delivers an input signal suitable to reduce or eliminate tremors, or to attain some other desired effect.

However, the process of mapping the brain can be a difficult one. It can be extremely difficult to discern neuronal spikes from background noise (and from any stimulating input pulses) within these data, particularly owing to the wide variety of characteristics neuronal spikes may have; spikes can vary widely in their shape, amplitude, period, frequency, and so forth. The same neuron can even generate different spike readings over time, both owing to variability in the neuron itself and owing to factors such as nearby pulsing blood vessels creating small changes in neuron-to-probe spacing. Experienced neurologists and others can over time gain skill in identifying the neuronal spikes of individual neurons from probe readings, but since probes may contain large arrays of reading microelectrodes, thereby generating multiple streams of reading data, it is virtually impossible for human operators to successfully process all of the generated data. It would therefore be useful to have improved methods available for identifying neuronal spikes, in particular methods which require minimal human review and supervision, and which might therefore be suitable for use in expert systems and other automated or semi-automated systems for probe data review.

SUMMARY OF THE INVENTION

The invention, which is defined by the claims set forth at the end of this document, is directed to methods and systems which at least partially alleviate the aforementioned problems. A basic understanding of some of the preferred features of the invention can be attained from a review of the following brief summary, with more details being provided elsewhere in this document.

After a series of microelectrode readings (i.e., sampled readings of amplitude/voltage over time) are obtained, the readings may (if desired) be cleansed of any artifacts arising from any stimulating input pulses that were delivered to the surrounding tissue, thereby allowing easier identification of any neuronal spikes. To remove artifacts, a detected artifact—whose timing can be relatively readily determined, either owing to the known timing of the stimulating input pulses and/or owing to the fact that stimulating input pulses tend to have higher amplitude than neuronal spikes—can be subtracted from any later artifacts detected in the readings, or an average of several artifacts can be subtracted from the artifacts in the microelectrode readings. However, it has been found that subtraction may not always efficiently remove artifacts from microelectrode readings, particularly where artifacts have high-frequency components. Thus, it is preferred that at high-frequency regions of artifacts in microelectrode data, the amplitudes of the microelectrode readings be "flattened"—that they simply be zeroed or otherwise attenuated. The remainders of the artifacts can then be removed from the microelectrode readings via subtraction. This process is exemplified, for example, by the accompanying FIGS. 4A and 4B, wherein FIG. 4A shows a series of raw or "uncleaned" microelectrode readings with plainly evident input pulse artifacts, and FIG. 4B shows the same series after flattening of the artifacts in the high-frequency regions denoted F and subtracting the artifacts in the low-frequency regions denoted S.

The microelectrode readings may then be reviewed to identify series of successive readings having continuously increasing amplitude (as might occur at the outset of a positive-amplitude peak of a neuronal spike) and/or continuously decreasing amplitude (as might occur at the outset of a negative-amplitude valley of a neuronal spike), with each such series of readings representing a spike candidate. It has been found that the probability distribution of several successive amplitudes constantly increasing (or decreasing) as a function of amplitude (e.g., of the first amplitude in the series) is a bimodal one which exhibits two peaks, one being at a lower amplitude and having a higher proportion of spike candidates, and the other being at a higher amplitude and having a lower proportion of spike candidates. The latter of these peaks represents a signal peak populated by neuronal spikes, and the former of these represents a noise peak, i.e., it does not contain neuronal spikes. This is illustrated in the accompanying FIGS. 6A-6C, which show (at the right) the amplitude distribution of candidate spikes at a variety of signal-to-noise ratios (FIG. 6A having lowest noise and FIG. 6C having the highest), with exemplary sections of microelectrode readings at these signal-to-noise ratios being depicted at left. Thus, neuronal spikes can be chosen from the spike candidates by excluding spike candidates which are clustered about a lower amplitude, and/or which are clustered about the most commonly occurring amplitude (i.e., by excluding those spike candidates situated in the noise peak). Conversely, neuronal spikes can be chosen from the spike candidates by including spike candidates clustered about a higher amplitude, and/or which are clustered about the second most commonly occurring amplitude (i.e., by including those spike candidates situated in the signal peak). A preferred method of identifying the spike candidates representing neuronal spikes is to look to the amplitude at the center of the noise peak (this amplitude representing the median amplitude, or at least approximately so, of the candidate spikes in the noise distribution), and then double this value to set a threshold amplitude value defining the nominal right tail of the noise distribution (and thus the nominal left tail of the signal distribution). Thus, spike candidates having amplitudes greater than this threshold amplitude value (greater than twice the median amplitude of the noise distribution/peak) can be regarded to be neuronal spikes.

In the foregoing method, it is preferred that the determination of whether increasing (or decreasing) slope is present, and thus whether microelectrode readings correspond to a spike candidate, be based on at least three points (i.e., three sampled microelectrode readings), and preferably no more than five points, at least when these points are chosen at a frequency of 25 kHz. Since the introductory upward and downward slopes of most neuronal spikes tend to be approximately 0.2 ms in duration or longer (see FIG. 9 for examples), it is preferred that slopes be tested by a series of points ranging over approximately 0.075-0.175 ms, or more preferably 0.1-0.15 ms.

After neuronal spikes are identified, it is then useful to assign them specific starting and ending times, since this can ease spike grouping (as described below) and/or other spike analysis activities. A preferred nominal starting point for a neuronal spike is at a zero crossing (point of zero amplitude) prior to the positive threshold amplitude value (assuming the spike starts with a positive peak), or prior to the negative threshold amplitude value (assuming the spike starts with a negative peak). Similarly, a nominal ending time can be assigned by locating a zero crossing after the negative or positive threshold amplitude value on the following negative or positive peak. Most preferably, the second zero crossings prior to and after the threshold values are chosen for use as the start and end of a neuronal spike, since these tend to adequately capture neuronal spikes without including excessive noise at the start and/or end of the spikes.

If desired, spikes may then be grouped by neuron so that one may determine how many neurons are present in a set of microelectrode readings, and may review the spike characteristics of each neuron. A preferred grouping method is to review all identified neuronal spikes in sequence, and with each one, compare its characteristics to those of "template" spikes (if any) stored in a database/library. If the spike meets the characteristics of the spike template to within a predefined tolerance, it is grouped with the spike template; if it does not, it is stored as a template against which later spikes may be compared. Preferably, the characteristics used for comparison between spikes and templates are time scaling (i.e., whether at least substantially identical time exists between the amplitude maxima and amplitude minima of the spike and the template against which it is being compared), and amplitude proportionality (i.e., whether the maxima and minima, or other specific points along the spike, are all proportionate to the corresponding values on the template to which the spike is compared). Other characteristics of spikes could also be used for comparison and grouping, e.g., root mean square amplitude of spikes, the differences between amplitude maxima and minima, etc.

Since this template-matching methodology effectively adopts the first-encountered member of any distinct group of spikes as a template for that group, the spike adopted as the template for the group may not necessarily represent the average spike within the group. Thus, it is also useful to store a running average of the spikes in a group so that this average can be used as a representative member of the group if/when needed.

Grouping, whether performed by template matching or by other methods, can also effectively assist with spike discrimination and artifact cleansing. For example, if groups of spikes include only a single or few neuronal spikes therein, this may indicate that the spikes in the group are not in fact neuronal spikes, but are rather noise spikes, and thus these may be excluded from the template/neuronal spike database. Conversely, if groups of spikes contain very large numbers of spikes, this may also indicate the presence of non-neuronal spikes which should be excluded—for example, if artifact cleansing is not performed, a very large group of spikes may arise wherein these spikes are in fact artifacts. The foregoing methods therefore provide a means for identifying neuronal spikes and sorting them according to their source (neuron) in a manner which needs no human intervention/supervision, and which can readily be implemented in computers, medical instrumentation, expert systems, and other devices for automatic (or substantially so) analysis of microelectrode readings. Further, the methods are computationally simple, and can be run in real time as microelectrode readings are collected, in addition to (or instead of) in stored collections of previously-obtained microelectrode readings. The methods are also well suited for the processing of very large amounts of microelectrode readings, such as those that are provided by probes with dense arrays of multiple microelectrodes thereon, and for which the collected data becomes so immense that it is practically unprocessable by systems requiring human supervision. Further advantages, features, and objects of the invention will be apparent from the following detailed description of the invention in conjunction with the associated drawings.

BRIEF DESCRIPTION OF THE DRAWINGS

FIG. 1 depicts an exemplary plot of microelectrode data (voltage versus time) as measured by a probe microelectrode within a brain, with the solid arrows indicating the time of stimulating input pulses delivered to the brain (and with the artifacts of these pulses, i.e., their measured output, being visible as large-amplitude spikes), and with the open arrows indicating the times of neuronal spikes.

FIG. 2A depicts the artifact of a stimulating input pulse delivered to the brain over a timescale which is expanded in comparison to the timescale of FIG. 1.

FIG. 2B depicts several stimulating input pulse artifacts from the same measurement session (as in FIG. 1) with the waveforms of all input pulse artifacts time-shifted to begin at the same time, showing that input pulse artifacts from the same measurement session can be substantially identical, and thus can be characterized to allow their removal from the measured microelectrode data.

In FIGS. 4A and 4B, FIG. 4A illustrates raw data (original measured microelectrode readings) with input pulse artifacts, and FIG. 4B then illustrates the same data after the artifacts are cleansed therefrom by use of the foregoing flattening and subtraction method (with flattening regions F and subtraction regions S again being shown).

FIG. 5 schematically depicts a method for discrimination of neuronal spikes from background noise within measured microelectrode readings, wherein a series of successive sampled microelectrode readings (here every other one of the sampled microelectrode readings) is tested to see whether a prolonged increase in amplitude occurs, thereby indicating the possible presence of a neuronal spike.

FIGS. 6A-6C then illustrate a series of measured microelectrode readings centered about a neuronal spike at a variety of signal-to-noise levels (with noise increasing from FIG. 6A-6C). An adjacent histogram shows the frequency of occurrence of a prolonged amplitude increase (such an amplitude increase being indicative of a "candidate neuronal spike") versus the amplitude of the candidate neuronal spikes, with such histograms showing a bimodal distribution wherein the peak at low amplitude is indicative of noise spikes and the peak (or "hump") at higher amplitude is indicative of neuronal spikes, and wherein the vertical lines in the histograms—set at twice the amplitudes of the noise peak—is set as a threshold above which neuronal spikes are assumed to occur. (Note that the plots of the measured microelectrode readings only represent a small portion of the data used to generate the histograms.)

FIG. 7 illustrates a method used to assign specific starting and ending times to a neuronal spike identified by use of the bimodal distribution of FIGS. 6A-6C, wherein the second zero crossing prior to the amplitude threshold of FIG. 6A (shown as T+) is assumed to be the start of the neuronal spike, and a second zero crossing after a negative amplitude threshold—which is calculated for negative-voltage portions of identified neuronal spikes similarly to FIG. 6A—is assumed to be the end of the neuronal spike.

FIG. 8 depicts a series of neuronal spikes emitted by the same neuron over time, with all neuronal spikes set to the same time datum, showing that the characteristics of the spikes from the same neuron tend to be substantially similar save for their amplitude scaling, and thereby implying that identified spikes which are similar save for amplitudes (but amplitudes being proportional) may be assumed to come from the same neuron.

FIG. 9 illustrates a series of representative (or template) neuronal spikes emitted by five different neurons, all shifted to the same time datum and rescaled to the same amplitude, illustrating the different characteristics of neuronal spikes emitted by different neurons.

DETAILED DESCRIPTION OF PREFERRED VERSIONS OF THE INVENTION

Figure 3:
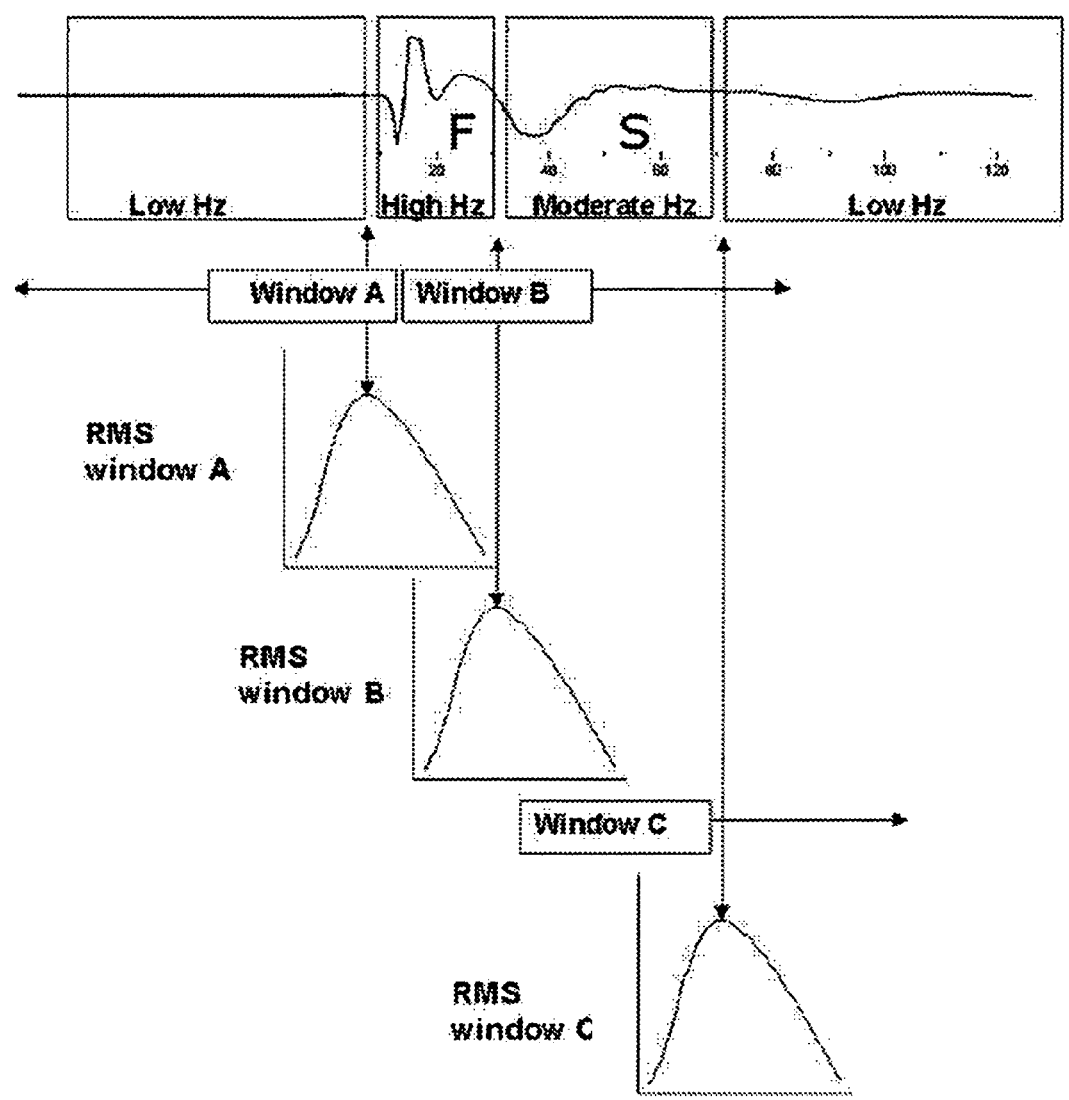
FIG. 3 schematically depicts a scheme for removal of input pulse artifacts from measured microelectrode data wherein measurements of the autopower are generated starting near the time of the delivery of the stimulating input pulse. Peaks in the autopower of the measured microelectrode readings (including the input pulse artifact) are then used to define a flattening region F wherein the microelectrode readings may be flattened (artificially attenuated), and also a subtraction region S wherein the values of a representative artifact may be subtracted from the measured microelectrode readings, with such flattening and subtraction resulting in removal of the artifact from the measured microelectrode readings.

I. Removal of Artifacts (e.g., Stimulus Input Pulse Artifacts)

As previously noted, when collecting readings from electrodes situated within the brain or other tissue, input voltage pulses can be simultaneously delivered to the tissue as a stimulus to provoke neuron firings (and thus detectable neuronal spikes). Since the electrode(s) on the probe which are to capture the readings of the neuronal spikes also often capture measurements of these stimulating input pulses, it can be useful to "filter" these stimulating input pulses from the captured probe microelectrode readings so that the stimulating input pulses are not mistaken for neuronal spikes, and so that one is left with a "clean" data train which effectively consists solely of neuronal spikes and background noise, thereby making identification of neuronal spikes easier. Following is a preferred series of steps used for the removal of artifacts of the stimulating input pulses from the captured microelectrode readings, though it should be understood that such removal is not mandatory (and similarly, other methods of artifact removal could be used, with the steps below merely being preferred). Additionally, while this discussion generally refers to the removal of artifacts of stimulating input pulses from microelectrode readings, it should be understood that the methodology described herein can be applied to other forms of repetitive and/or timed artifacts.

FIG. 1 illustrates a representative waveform created by a series of captured microelectrode readings (i.e., sampled measurements of microelectrode readings), plotted as voltage over a span of time, with stimulating input pulses—actually their artifacts, i.e., the stimulating input pulses as read by the microelectrode (rather than as delivered by their emitter)—being depicted at the solid arrows, and neuronal spikes (as later detected by the discrimination method described later in this document) being depicted at the open arrows. Here the captured microelectrode voltage readings were sampled from the brain at 25,000 Hz. FIG. 2A then shows a stimulating input pulse with enlarged time scale (in milliseconds) and compressed amplitude scale. The amplitude scale is centered about zero because a filter is used to remove any DC offset component from the captured microelectrode readings, but it should be understood throughout this document that "zero" or datum voltages for microelectrode readings could in fact be nonzero. Note that while each stimulating input pulse used in the examples of FIGS. 1 and 2A is nominally a square wave input, its artifact exhibits a radically different shape owing to RC (resistive-capacitive) effects within the tissue between the stimulating input pulse emitter and the probe microelectrode capturing the artifact. (Also note that stimulating input pulse shapes other than square waves may be used, and thus differently-shaped artifacts can result.) FIG. 2B then illustrates a plot similar to FIG. 2A, but with many successive artifacts of successive square wave stimulating input pulses reset to the same time datum, thereby superimposing the artifacts. This shows that input pulse artifacts are substantially identical over time: so long as substantially identical stimulating input pulses are delivered to the tissue, substantially identical resultant artifact pulses can be measured. Thus, the problem becomes one of characterizing the artifact pulses and then filtering these artifact pulses out of the captured microelectrode readings so as to obtain a "clean" set of microelectrode data readings, from which neuronal spikes can be identified.

Since the stimulating input pulses (and thus their artifacts) have known and regular timing—the timing of the stimulating input pulses being computer-controlled—one could simply measure an artifact pulse (or average a series of artifact pulses) and then repeatedly subtract the pulse(s) from the captured microelectrode reading data at the expected time of each artifact pulse. (Also note that artifact pulses tend to have substantially higher amplitude than the surrounding noise and neuronal spikes, so in cases where input pulse timing is unknown, artifact subtraction/removal could alternatively be timed to occur with respect to the detection of such large-amplitude readings.)

However, such subtraction methods do not clean the microelectrode data readings as well as desired since there is some small variation between artifact pulses. In particular, the timing of the sharp transients (sharp voltage rise/fall) at the outset of an artifact—the initial negative and positive humps in FIG. 2A and FIG. 2B—can vary, and thus subtraction of a representative or averaged artifact pulse from the successive artifact pulses in the captured microelectrode readings will not always result in complete removal of artifact pulses. Since any remaining non-subtracted portions of the artifact pulses could potentially be mistaken for a neuronal spike, it is useful to enhance such subtraction methods, and the following steps are preferred.

After locating artifact pulses in the captured microelectrode readings, the sharp transients therein can be identified, and the amplitudes of the artifact pulses over the timespan of the transients can be set to zero to "flatten" the transients. The subtraction method can then be performed over the remainders of the artifacts. A preferred method of identifying a transient region to be flattened is to look to the captured microelectrode readings at the time corresponding to the emission of a stimulating input pulse, and then move forward in time over the captured microelectrode readings, calculating the autopower of the readings. Peaks in the RMS value of the autopower will appear at the nominal start and ending points of the transient (high frequency) region to be flattened. Autopower RMS peaks will also occur at the nominal starting point of the low-frequency region of the artifact pulse which is merely to be subtracted (this starting point corresponding to the ending point of the transient region), and also at the nominal ending point of the low-frequency region (which also corresponds to the nominal end of the artifact). Thus, the RMS peaks bracket the nominal transient region to be flattened within the artifact (schematically represented in FIG. 3 by the region "F"), and also bracket the nominal low-frequency region to be subtracted within the artifact (schematically represented in FIG. 3 by the region "S"). FIG. 4 then illustrates exemplary results of such flattening and subtraction: in the flattened region, the captured microelectrode values are replaced by zero values (with the captured values at these flattened regions preferably being stored rather than simply discarded), and in the subtracted region, a representative or averaged artifact pulse is subtracted from the captured microelectrode readings. The result is a series of captured microelectrode readings which are substantially free of the effects of input pulse artifacts, thereby leaving a data train which should substantially consist only of neuronal spikes and background noise.

If the amplitudes at the edges of the flattening and/or subtraction regions are not zero, flattening and subtraction might result in an abrupt transition that could be mistaken for a neuronal spike. Consequently, it is useful to move the starting and end points of the aforementioned flattening and/or subtraction regions to nearby zero crossings (points of zero microelectrode data reading amplitude), as by expanding the start of the flattening region to the nearest zero crossing prior to the start of the nominal flattening region, and extending the end of the subtraction region to the nearest zero crossing following the end of the nominal subtraction region.

The subtraction step is effectively a filtration feature which removes the artifact (or at least its low frequency tail component) from the captured microelectrode readings while leaving any background noise and/or neuronal spikes over the corresponding time period, whereas the flattening step effectively eliminates sections of captured microelectrode reading data over the high frequency time period by replacing these data with zero values (though as noted previously, it is preferred that the captured microelectrode readings in the flattened regions be stored rather than simply discarded). Thus, flattening has the potential to destroy, distort or obscure neuronal spikes that may have occurred at the same time as an artifact pulse, such that the neuronal spike and the artifact pulse are superimposed in the captured microelectrode readings. However, the losses of neuronal spike data owing to flattening should be relatively minor: in general, only a few neuronal spikes (if any) should be lost. Additionally, most commonly-used stimulating input pulses result in transients (and thus flattening regions) of sufficiently short duration that flattening will only remove a small section of a neuronal spike in those instances where flattening coincides with a neuronal spike. In this instance, the computer or other instrument performing the data cleaning and spike identification can note the coincidence and "flag" the spike for reconstruction, as by reprocessing this section of data using only subtraction and no flattening (and using the stored data over the flattened region), and/or by fitting a spline across the missing portion of the neuronal spike. Note that in general, at the time of data cleansing/artifact removal, the locations of spikes will not yet be known; thus, such reconstruction would occur after spikes are identified, as by use of the discrimination method described below.

II. Discrimination of Neuronal Spikes

After the captured microelectrode reading data is cleaned (assuming cleaning is performed, this being an optional step), the next step is to determine when neuronal spikes occur within the data so that they may be isolated for further review. The preferred method for identifying spike occurrence utilizes some number of successive (in time) microelectrode readings in the captured microelectrode readings:

$$a_i, a_{i+1}, \ldots a_{i+n}$$

wherein n is a finite integer (n being greater than or equal to 2). Neuronal spikes are then identified on two bases:

(A) Neuronal spikes generally have greater amplitude than noise "spikes" (assuming a reasonable signal to noise ratio, such as those provided by high-quality microelectrode probes and reading/recording equipment).

(B) For a given (positive) amplitude $a_i$, the probability that all of the selected readings are successively increasing:

$$a_i < a_{i+1} < \ldots < a_{i+n} \quad (1)$$

is, in general, greater for neuronal spikes than for noise (i.e., there is a high probability that a neuronal spike meets the foregoing relationship, whereas most noise "spikes" have a low probability of meeting the foregoing relationship). As will be discussed later in this document, the converse is true for negative amplitudes $a_i$, i.e., a prolonged decrease in amplitude can be indicative of a neuronal spike. This is particularly true as n grows larger, and also as the selection rate for choosing the selected microelectrode readings from the captured microelectrode readings get smaller (slower).

To illustrate the application of these principles, FIG. 5 shows an exemplary segment of microelectrode data readings which include a neuronal spike, with the applicability of expression (1) being graphically illustrated on the positive introductory slope of the neuronal spike with n=2. Note that the amplitude (both positive and negative) of the neuronal spike is noticeably greater than that of the surrounding noise.

To further illustrate, FIGS. 6A-6C depict plots of representative sections of data sets of captured microelectrode readings having various signal to noise ratios (with the "signal," a neuronal spike, being centered in the plots). These are shown alongside incidence histograms for the captured microelectrode reading data from which the plots were taken, wherein the incidence of expression (1) being true is plotted versus the amplitude of $a_i$. It is seen that the incidence distribution of expression (1) being true as a function of the $a_i$ amplitude follows a bimodal Gaussian distribution, with one peak (the one with the lower amplitude $a_i$) primarily corresponding to noise "spikes," and the other (the one with higher amplitude $a_i$) primarily corresponding to neuronal spikes. Thus, one should be able to discriminate neuronal spikes from surrounding noise in the captured microelectrode readings by simply looking to the spikes in the microelectrode reading data which correspond to the second (higher amplitude $a_i$) peak. However, note that the signal (neuronal spike) and noise distributions overlap, with separation being greater with higher signal-to-noise ratio (with FIG. 6A having the greatest signal-to-noise ratio and FIG. 6C having the lowest). Therefore, there is a question of where to distinguish between the end of the noise peak and the start of the signal (neuronal spike) peak, and it is useful to set a discrimination threshold value which discriminates between signal and noise. A reasonable approximation for the discrimination threshold of the "tail" or right end of the noise distribution is to identify the maximum amplitude $a_i$ in the noise peak (this maximum amplitude $a_i$ corresponding, at least approximately, to the median of the amplitudes $a_i$ in the noise distribution), and then set the discrimination threshold at (for example) twice this value (indicated by the vertical lines T+ in the incidence histograms of FIGS. 6A-6C). In other words, the length of the left tail of the noise distribution (the left tail assumed to extend from zero amplitude to the maximum amplitude $a_i$ in the noise peak) is used to determine the (nominal) right end of the noise distribution (and thus the nominal left end of the signal distribution), by simply doubling the size of the left tail. However, other discrimination thresholds between the noise and neuronal spike distributions could be used if desired, e.g., rather than defining the tail of the noise distribution and assuming this to be the discrimination threshold for the signal (neuronal spike) distribution, one could instead identify the maximum amplitude $a_i$ in the signal peak, and then define some lower discrimination threshold for the signal distribution based on a fraction of this maximum amplitude. As another alternative, the discrimination threshold could be situated at some amplitude $a_i$ at some predefined location between the noise and signal peaks (e.g., halfway between the two).

It is notable that expression (1) is not the only criterion that may be used for identifying neuronal spikes. Looking to expression (1), and also looking to the shape of the neuronal spikes in FIGS. 6A-6C, it should be understood that expression (1) is effectively intended to identify neuronal spikes by seeking captured microelectrode readings with prolonged upward slopes (which are characteristic of the initial rises in the neuronal spikes depicted in FIGS. 6A-6C), and wherein these slopes are not so great as the sharp slopes characteristic of noise peaks (which are generally created by high-frequency, and thus high-slope, noise). It is preferred that microelectrode probes and reading equipment capable of obtaining signal-to-noise rations of 2.5 or more be used to capture microelectrode readings, since (as exemplified by FIG. 6A) it is then far easier for the methodology to pick out neuronal spikes. Below signal-to-noise ratios of 2.5, it is possible that some noise spikes may be misidentified as neuronal spikes, with misidentification becoming quite frequent at signal-to-noise ratios of approximately 1.5 and lower.

Additionally, if microelectrode readings are sampled/captured at higher sampling rates (and if they are similarly selected for testing versus expression (1) at higher rates), it may be useful to increase the number of points selected (i.e., n in expression (1) should also increase). Otherwise, the selected points used to test for the presence of expression (1) may exist across such a small expanse of the readings that the selected points are not as representative of a prolonged increase (or decrease) in slope. As previously noted, the use of three points for use in expression (1), selected at 25 kHz, has been found to be suitable; which translates to a selection of points spanning 0.12 ms. Thus, it is expected that suitable results should be obtained so long as slope is tested over a range of points extending over 0.1-0.15 ms.

Also note that the foregoing methodology identifies neuronal spikes on the basis of their initial prolonged upward slopes, but the neuronal spikes shown in FIGS. 6A-6C have other characteristics that could also or alternatively be used for identification. As an example, a neuronal spike might also or alternatively be identified on the basis of its downward drop following the initial rise of the spike, in which case the method could seek a prolonged downward slope (i.e., :$a_i > a_{i+1} > \ldots > a_{i+n}$). Additional characteristics could also be used to screen spikes, e.g., $a_i$ must cross from positive to negative for the spike to be a candidate for a neuronal spike, and/or the downward slope must immediately follow an upward slope. A particularly preferred method is to identify neuronal spikes by seeking selected positive microelectrode readings with prolonged upward slopes (i.e., which meet expression (1)), and which are then followed by negative microelectrode readings with prolonged downward slopes—in essence, by looking for the positive and negative "humps" of a neuronal spike.

So that the identified neuronal spikes are more concretely defined, it is then useful to define precisely when an identified spike begins and ends. A preferred way to do this is to look to an identified neuronal spike and locate the time at which its amplitude first crosses the (positive) discrimination threshold T+ (as discussed above), and then "look back" in time to the second zero crossing before this time. This is then assumed to be the start of the neuronal spike. Similarly, assuming that the neuronal spike is identified both by its first upward slope with positive amplitude (i.e., by expression (1)) and also by its first downward slope with negative amplitude, the second zero crossing after the time at which the spike first crosses the negative discrimination threshold can be assigned as the nominal end of the spike. This process is illustrated for an exemplary neuronal spike in FIG. 7, wherein the positive and negative thresholds are depicted at T+ and T−; the beginning of the neuronal spike was nominally set to the second zero crossing before the positive hump crossed the positive threshold crossing (this second zero crossing being indicated by the solid arrow), and the end of the neuronal spike was nominally set to the second zero crossing after the negative hump crossed the negative threshold crossing (this second zero crossing being indicated by the dashed arrow). The first zero crossings could be used instead, but this can truncate small amounts of the actual neuronal spike. Similarly, the definition of a neuronal spike could be extended outwardly to the third zero crossings, but this appears to at least occasionally incorporate unwanted noise at the starting and ending portions of the spike.

II. Grouping of Neuronal Spikes

Once neuronal spikes are identified, it is useful to group them so that one can determine whether selected sets of spikes came from the same or different neurons. If the different spikes measured at different tissue depths by different microelectrodes are sorted into groups (each group relating to a specific neuron), one can generate a detailed map of the tissue: one will know that at certain tissue depths, one may expect some number of detected neurons having measured spike characteristics.

One difficulty in grouping neuronal spikes into sets, with each set corresponding to a given neuron, is that the same neuron can (and often does) emit spikes which have highly variable characteristics (spike amplitudes in particular being highly variable). In the preferred grouping method described below, neuronal spikes are grouped in accordance with at least two characteristics: their timing matches (whether timing of factors such as spike start, amplitude maximum, and amplitude minimum are at least substantially identical between neuronal spikes), and amplitude scaling (whether the amplitude maxima and minima are proportionately scaled between different neuronal spikes). Upon review of numerous microelectrode readings, it was found that the timing characteristics of neuronal spikes emitted by a given neuron are relatively constant, in particular the time between the maximum and minimum of the spike. Also, amplitudes between different neuronal spikes emitted from the same neuron tend to be scaled: if the maximum of a first spike emitted by a given neuron is greater than the maximum of a second spike emitted by the same neuron, the minimum of the first spike also tends to be proportionately lesser than the minimum of the second spike. Further, such amplitude proportionality tends to extend throughout the entire periods of spikes emitted by the same neurons. These features are illustrated in FIG. 8, which show several neuronal spikes captured from the same neuron: while the amplitudes change between spikes, the time interval between features such as the maximum and minimum amplitudes does not, and all spikes appear similar save for their amplitude scaling. Thus, the various neuronal spikes identified from microelectrode readings may be grouped in accordance with these characteristics to identify spikes coming from the same neuron. If desired, additional characteristics can also be used to further refine grouping, as discussed below.

To group neuronal spikes, the computer (or other device performing the grouping) can start with the first identified neuronal spike and store it as a template against which later neuronal spikes can be compared, using at least the foregoing characteristics of timing matches and amplitude scaling. This process is then repeated with the next identified neuronal spike: if its characteristics fall outside the tolerances of the characteristics for a previous template, the spike is considered to correspond to a new neuron, is labeled as a new template, and is added to the library (database) of templates. On the other hand, if a neuronal spike does have characteristics matching those of a template within some predefined tolerance—say, if maximum/minimum timing matches within 5%, and if maxima and minima are proportionate to within 5%—the neuronal spike is considered to be a reoccurrence of a neuronal spike of the neuron associated with the template, and is grouped with the template spike that it matches. The process is continued until all identified spikes are defined as templates or grouped with an already-identified template.

This template-matching method would not be able to distinguish a spike from a new neuron (i.e., a new type of neuronal spike which does not match any prior templates) from the superimposition of two simultaneously occurring neuronal spikes. However, given the relative frequencies of neurons at a single microelectrode recording site using high-impedance, small-tipped microelectrodes, the occurrence of superimpositions is likely to be rare. Nevertheless, if a new type of neuronal spike occurs at low frequency—e.g., 1 Hz or less—these could be excluded from further analyses on the basis that it may be a superimposition of multiple neuronal spikes. In similar respects, if the method results in groups containing only a single neuronal spike (this single spike thereby defining the template for the "group" in question), or very few spikes, these groups/templates might be discarded under the assumption that they are superimposed spikes or other forms of aberrational data (e.g., noise spikes). These measures imply that grouping can in effect assist with spike identification: if identified spikes are assigned to groups with a single or very few members in their group (i.e., if the spike was identified as occurring only once or a very few times), it might be identified as other than a neuronal spike and can be excluded from the template/spike library.

Since the foregoing method stores as a template the first-encountered neuronal spike having unique characteristics, there is a question as to whether the template is truly representative of the neuron: was the neuronal spike chosen as its template an "average" firing of the neuron, or was it a particularly strong or weak one, or one which is otherwise non-representative? A group of spikes could be averaged to serve as the template, but over time such averaging could result in a "migration" of the template. Thus, it is preferred to simply store the first-encountered novel neuronal spike as the template for matching/grouping subsequent neuronal spikes, and to create a separate running average neuronal spike for each group. This avoids migration of the template parameters, and at the same time the template itself is not altered and therefore does not migrate. However, the averaged neuronal spike can provide a more representative depiction of the group than the template.

To further explain the impact of the possibility that a template spike may not be representative of its neuron, consider the case where the first-encountered neuronal spike having unique characteristics, and which is therefore designated as a template, might possibly be from one extreme of the distribution of all neuronal spikes from the same neuron. The next neuronal spike from the same neuron may be at the other extreme of the distribution. In this case, the characteristics of the spikes may not match to the set tolerances, and therefore the spikes may each be assigned as different templates despite the fact that they are from the same neuron. By storing a running average of the spikes within each template's group, the running averages of the groups should over time converge toward each other as each becomes more representative of the neuron. Then, to reduce the possibility of this "template misassignment," the foregoing template-matching method can be performed again, but this time using the running averages as the templates. As a result, any misassigned templates (i.e., templates corresponding to the same neuron, but which previously went unmatched owing to their status as outliers) will be combined within the same groups, thereby eliminating redundant templates for the same neurons.

To illustrate the different forms that templates may assume, FIG. 9 shows templates from five neurons recorded at a single site in the motor cortex. To ease comparison of spike shapes, the templates have been rescaled to have the same minimum value, and have been shifted in time so that the times of the amplitude minima are the same. It is seen that the templates from each neuron (and their neuronal spikes in general) are indeed different from the others.

The designation of neuronal spikes as template spikes, and the matching of spikes to templates, can also use additional (or alternative) characteristics besides timing matches and amplitude scaling. As examples, neuronal spikes may be designated templates if their maxima and/or minima, or the distance in amplitude therebetween, differs from that of any prior template by some amount (and later neuronal spikes may be matched to this template, and thus assigned to the same neuron, if their maxima and/or minima, or the distance therebetween, matches that of the template within some tolerance). Similarly, a neuronal spike may be designated as a template if its RMS amplitude (or the RMS amplitude of some portion of the spike) differs from that of any prior templates by some amount, and later neuronal spikes may be grouped with this template if their RMS amplitude matches that of this template within some tolerance. Other amplitude characteristics, such as proportions between the amplitudes of different humps, are also possible. Additionally or alternatively, neuronal spikes may be designated as templates or matched to templates on the basis of timing characteristics such as the time between maxima and minima, or between the spike start and maximum (and/or minimum). While these characteristics are to some degree redundant of the characteristics of amplitude scaling (which considers amplitude characteristics) and timing matches (which considers timing characteristics), they can nonetheless contribute to more specific template designation and/or matching. Characteristics which combine amplitude and time features, such as instantaneous slopes calculated at some portion along the spike's period, could also be used.

The use of more characteristics to match spikes to templates does bear greater risk that some neuronal spikes from the same neuron may be assigned to (and matched with) different templates (i.e., they will be assumed to emanate from different neurons). However, if template matching is repeated using the running average method discussed above, neuronal spikes which seemingly come from different neurons may be reassigned to fewer templates, thus eliminating redundancies.

IV. Conclusion

Exemplary versions of the invention have been reviewed above to illustrate preferred methodologies and how to implement them. However, it should be understood that since the foregoing methodologies are merely examples, many variations from the foregoing arrangements are possible. Following is an exemplary list of modifications to the foregoing arrangements.

Initially, it is emphasized that the artifact removal methods (Section I of this document), spike discrimination methods (Section II of this document), and spike grouping methods (Section III of this document) need not all be implemented in the same data analysis session or data analysis system. As an example, artifact removal and/or spike grouping need not be performed, and microelectrode readings could simply be analyzed for the presence of spikes by use of the discrimination methods. As another example, libraries of spike data already in existence (i.e., which have no use for the discrimination methods) can be analyzed by use of the grouping methods of Section III to identify the neurons involved with each spike.

Elements and functions of the artifact removal, spike discrimination, and spike grouping methods can also be combined, or used at times other than (or for purposes other than) those described. As one example of how an element of one of the methods may be used in another of the methods, consider that the spike discrimination method of Section II described an optional step wherein the beginning and end of a neuronal spike are identified. This step could instead be used in the spike grouping method of Section III. For example, if the invention is implemented solely by applying the spike grouping method to libraries of spike data already in existence, it may be useful to define the beginnings and ends of the already-identified spikes so that template definition and matching is performed on well-defined spikes.

As another example, consider that Section I of this document described how the artifacts of stimulating input pulses may be cleaned from the electrode readings before spikes are identified within such readings. However, it is also possible that the artifacts can be left in the readings, identified as spikes as per Section II of this document (albeit not neuronal ones), and can then be grouped as per Section III, at which point their group(s) can be eliminated from the data pool. In other words, the artifacts from the stimulating input pulses can be treated as neuronal spikes, and once they are identified as coming from specific "neurons"—these neurons actually being the input electrode(s) or other source of the stimulating input pulses—they can be ignored. Thus, if desired, the removal of stimulating input pulses can occur as a later or final step in spike identification, rather than as a first or earlier step.

Further, any of the features of artifact removal, spike discrimination, and/or spike grouping as described above could be used with artifact removal, spike discrimination, and/or spike grouping methods other than those described in this document. As one example, grouping could instead be performed by use of the clustering methods described in U.S. provisional patent application 60/638,509, entitled "Methods and devices for analysis of clustered data, in particular action potentials (i.e., neuron firing signals in the brain)," which is the subject of a copending United States utility patent application (and which is hereby incorporated by reference, such that it should be regarded as part of this document). Other methods of artifact removal, spike discrimination, and spike grouping that might be usable are set out in references cited in an Information Disclosure Statement accompanying the patent application that resulted in this document, and these references should be listed in any "References Cited" section set out at the outset of this document.

While the invention has generally been described as useful for identification and classification of neuronal spikes (extracellular action potentials or ECAPs) in the brain, it is expected that the methodologies described in this document may also be useful for the analysis of other physiological signals of a similar nature, e.g., cardiac monophasic action potentials (MAPs).

The invention is therefore not intended to be limited to the preferred versions of described above, but rather is intended to be limited only by the claims set out below. Thus, the invention encompasses all different versions that fall literally or equivalently within the scope of these claims.

What is claimed is:

1. A method of identifying neuronal spikes comprising the steps of:
   a. obtaining amplitude readings sampled over time from an electrode situated within tissue;
   b. identifying series of successive readings having at least one of
      (1) continuously increasing amplitude, and
      (2) continuously decreasing amplitude, each such series of readings representing a spike candidate;
   c. identifying spikes within the spike candidates, the spikes being chosen from the spike candidates having greatest amplitude; and d. performing at least one of the steps of:
   (1) placing a therapeutic electrode within the tissue, and
   (2) delivering electrical stimulation from a therapeutic electrode to the tissue, in dependence on the identified spikes.

2. The method of claim 1 wherein the step of identifying spikes within the spike candidates includes the step of choosing as spikes at least some of the spike candidates having amplitudes greater than the most frequently occurring amplitudes of the spike candidates.

3. The method of claim 2 wherein the spike candidates chosen as spikes have amplitudes at least twice as great as the most frequently occurring amplitudes of the spike candidates.

4. The method of claim 1 wherein each series of successive readings includes at least three readings.

5. The method of claim 1 wherein the step of identifying spikes within the spike candidates includes the step of:
   a. identifying the lowest amplitude about which the greatest number of spike candidates occur;
   b. setting a spike threshold amplitude greater than this lowest amplitude;
   c. identifying as spikes at least some of the spike candidates having amplitudes greater than the spike threshold amplitude.

6. The method of claim 5 further comprising the step of assigning a start time to each identified spike, each spike having a start time corresponding to a zero amplitude for the spike occurring prior to the time when the spike attains the spike threshold amplitude.

7. The method of claim 6 where the start time corresponds to the second zero amplitude occurring prior to the time when the spike attains the spike threshold amplitude.

8. The method of claim 1 wherein the step of identifying spikes within the spike candidates further includes the steps of:
   a. identifying the two largest groups of spike candidates wherein:
      (1) each group has at least substantially similar amplitude; and
      (2) one group has larger amplitude than the other;
   b. choosing as spikes at least some of the spike candidates in the group having larger amplitude.

9. The method of claim 1 wherein the step of identifying spikes within the spike candidates further includes the steps of:
   a. identifying two groups of spike candidates wherein:
      (1) each group has high incidences of spike candidates with at least substantially similar amplitudes, and
      (2) one group has a median amplitude at least twice as great as the median amplitude of the other group; and
   b. choosing as spikes at least some of the spike candidates in the group having the median amplitude at least twice as great as the median amplitude of the other group.

10. The method of claim 1 further comprising the step of grouping the spikes, each group having:
    (1) at least substantially identical time between the amplitude maxima and amplitude minima of the spikes therein, and
    (2) proportionate amplitude maxima, and also proportionate amplitude minima, between the spikes therein.

11. The method of claim 10 wherein each group also has at least one of:
    (1) amplitude maxima,
    (2) amplitude maxima,
    (3) the differences between amplitude maxima and minima, and
    (4) root mean square amplitude,
    matching to a predefined tolerance.

12. The method of claim 10 further comprising the step of generating, for each group of spikes, average values of at least some of the data of the spikes in the group.

13. The method of claim 1 wherein spike candidates are defined by series of successive readings having at least one of
    a. continuously increasing amplitude, and
    b. continuously decreasing amplitude,
    wherein each such series extends over a period between approximately 0.075-0.175 ms.

14. A method of identifying neuronal spikes comprising the steps of:
    a. obtaining amplitude readings sampled over time from an electrode situated within tissue;
    b. identifying series of readings wherein a positive-amplitude peak is followed by a negative-amplitude valley, each such series of readings representing a spike candidate;
    c. determining the amplitude distribution of the spike candidates;
    d. identifying the amplitude within the distribution at which the highest proportion of spike candidates are clustered, this amplitude representing a noise peak;
    e. selecting as spikes at least some of the spike candidates having amplitudes greater than the amplitude of the noise peak; and
    d. performing at least one of the steps of:
       (1) placing a therapeutic electrode within the tissue, and
       (2) delivering electrical stimulation from a therapeutic electrode to the tissue, in dependence on the spikes.

15. The method of claim 14 wherein the spike candidates selected as spikes have amplitudes at least twice as great as the amplitude of the noise peak.

16. The method of claim 14:
    a. further comprising the step of identifying the amplitude within the distribution at which the second highest proportion of spike candidates are clustered, this amplitude representing a signal peak; and
    b. selecting as spikes spike candidates situated about the signal peak.

17. The method of claim 14 further comprising the step of assigning a start time to each spike, each spike having a start time corresponding to a zero amplitude for the spike occurring prior to the time of the spike's positive-amplitude peak.

18. The method of claim 14 further comprising the step of assigning an end time to each spike, each spike having an end time corresponding to a zero amplitude for the spike occurring after to the time of the spike's negative-amplitude peak.

19. The method of claim 14 further comprising the step of grouping the identified spikes, each group having:
    a. at least substantially identical time between the amplitude maxima and amplitude minima of the identified spikes therein, and
    b. at least one of:
       (1) proportionate amplitude maxima between the spikes therein, and
       (2) proportionate amplitude minima between the spikes therein.

20. The method of claim 19 further comprising the step, for each group, of calculating an average of at least some of the data contained within the spikes in the group.

21. The method of claim 19 further comprising the steps of:
    a. identifying groups having at least a minimum number of spikes therein as containing signal spikes, and b. identifying groups having less than the minimum number of spikes therein as containing noise spikes.

22. A method of identifying neuronal spikes comprising the steps of:
   a. obtaining amplitude readings sampled over time from an electrode situated within tissue, the amplitude readings defining spikes;
   b. grouping at least some of the spikes, each group having:
      (1) at least substantially identical time between the amplitude maxima and amplitude minima of the spikes therein,
      (2) proportionate amplitude maxima between the spikes therein, and
      (3) proportionate amplitude minima between the spikes therein; and
   d. performing at least one of the steps of:
      (1) placing a therapeutic electrode within the tissue, and
      (2) delivering electrical stimulation from a therapeutic electrode to the tissue,
      in dependence on the grouped spikes.

23. The method of claim 22 further comprising the step of calculating, for each group, an average of at least some of the data of the spikes within the group.

24. The method of claim 22 further comprising the step of identifying each group as being:
   a. a signal spike corresponding to a neuronal firing, or
   b. a noise spike which does not correspond to a neuronal firing,
   at least partially on the basis of the number of spikes within each group.

25. The method of claim 22 wherein the amplitude readings include signal spikes and noise spikes.

26. The method of claim 25 further comprising the step of identifying the signal spikes by:
   a. identifying series of amplitude readings wherein a positive-amplitude peak is followed by a negative-amplitude valley, each such series of readings representing a spike candidate;
   b. determining the amplitude distribution of the spike candidates;
   c. identifying the amplitude within the distribution at which the highest proportion of spike candidates are clustered, this amplitude representing a noise peak;
   d. selecting as spikes at least some of the spike candidates having amplitudes greater than the amplitude of the noise peak.

27. The method of claim 25 further comprising the step of identifying the signal spikes by:
   a. identifying series of amplitude readings wherein a positive-amplitude peak is followed by a negative-amplitude valley, each such series of readings representing a spike candidate;
   b. determining the amplitude distribution of the spike candidates;
   c. identifying the two different amplitudes within the distribution at which the highest proportions of spike candidates are clustered, the lower of these amplitudes representing a noise peak and the higher of these amplitudes representing a signal peak;
   d. selecting as spikes at least some of the spike candidates having amplitudes about the signal peak.

* * * * *